United States Patent [19]

Hechenbleikner et al.

[11] 3,970,532
[45] July 20, 1976

[54] 2-HYDROXYETHYLPHOSPHINES

[75] Inventors: Ingenuin Hechenbleikner, West Cornwall; William Palmer Enlow, Falls Village, both of Conn.

[73] Assignee: Borg-Warner Corporation, Chicago, Ill.

[22] Filed: Jan. 16, 1975

[21] Appl. No.: 541,542

[52] U.S. Cl............... 204/158 R; 260/488 F; 260/491; 260/606.5 P
[51] Int. Cl.² ............... B01J 1/10; B01J 1/12
[58] Field of Search ........ 260/606.5 P, 488 F, 260/491; 204/158 R

[56] References Cited
UNITED STATES PATENTS

| | | | |
|---|---|---|---|
| 2,584,112 | 2/1952 | Brown | 260/606.5 P |
| 2,803,597 | 8/1957 | Stiles | 204/158 R |
| 2,957,931 | 10/1960 | Hamilton et al. | 260/606.5 P |
| 3,242,217 | 3/1966 | Hammann et al. | 260/606.5 P |
| 3,435,076 | 3/1969 | Mason | 260/606.5 P |
| 3,489,811 | 1/1970 | Drucker et al. | 260/606.5 P |
| 3,657,352 | 4/1972 | Kleiner | 260/606.5 P |
| 3,663,729 | 5/1972 | Tavs | 260/606.5 P |

FOREIGN PATENTS OR APPLICATIONS 673,451  6/1952  United Kingdom

OTHER PUBLICATIONS

Chemical Abstracts, vol. 56, 15541–15543 (1962).
Chemical Abstracts, vol. 57, 15145c (1962).
Stiles, J.A.C.S., vol. 74, 3282–3284 (1952).

Primary Examiner—Helen M. S. Sneed
Attorney, Agent, or Firm—Joseph Shekleton

[57] ABSTRACT

A process for the preparation of 2-hydroxyethylphosphines. The process involves the addition of an alkenyl carboxylate (such as vinyl acetate) to a phosphine containing a P—H bond, followed by conversion of the resulting ester-substituted phosphine to the corresponding 2-hydroxyethylphosphine. The conversion is effected by alcoholysis or by hydrolysis.

8 Claims, No Drawings

2-HYDROXYETHYLPHOSPHINES

This invention relates to a method for preparing 2-hydroxyethylphosphines. Moe particularly, it relates to such a method which utilizes the corresponding 2-acetoxyethylphosphine as a starting material. STill more particularly, it may also involve preparation of that 2-acetoxyethylphosphine from a phosphine containing a P-H bond, i.e., phosphorus-to-hydrogen.

Because of their phosphorus content and their active hydroxyl group, the 2-hydroxyethylphosphines of this invention are useful as starting materials in the preparation of flame-retardant materials. They are useful also as starting materials in the preparation of phosphine oxides and sulfides which are in turn useful in water-based lubricants. The bis- and trishydroxyethylphonsphine can also be reacted with aryl polyisocyanates to give useful polyurethane resins.

In 1952, U. K. Patent No. 673,451 was published showing the reaction, in general, of phosphines with olefinic compounds. Specifically shown is the reaction of phosphine with allyl alcohol to give 3-hydroxypropylphosphine plus the corresponding bis- and tris-substituted phosphines.

A similar teaching is found in Stiles et al., *J. Am. Chem. Soc.*, 74, 3282 (1952).

The hydrolysis of an ester of a bis-hydroxytrimethylenephosine oxide is shown in C.A. 57, 15145c (1962). The hydrolysis product is the expected bis-hydroxytrimethylenephosphine oxide.

Hammam et al., in U.S. Pat. No. 3,242,217, show the hydrolysis of a tribenzoate and trilaurate of a phosphinylidynetrimethanol to obtain

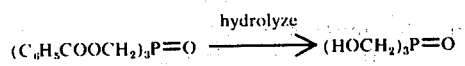

the desired phosphinylidynetrimethanol.

The preparation of 2-hydroxyethylphosphines has been accomplished, in certain instances, by reaction of a phosphine with ethylene oxide but this is an unsatisfactory method because of the tendency of the ethylene oxide to form a polyoxyethylene chain. The inevitable result is a mixture of products from which it is very difficult to separate and purify the desired 2-hydroxyethylphosphine.

Another method of preparation has involved the reaction of phosphine with an alkyl vinyl ether, followed by cleavage of the ether group, but this likewise is not a satisfactorily efficient method.

The prior art above does not show how to prepare 2-hydroxyethylphosphines by way of a convenient process which yields relatively pure product and, furthermore, the methods of synthesis shown in that art are not obviously applicable to such preparation.

It is accordingly a principal object of the present invention to provide a process for the preparation of 2-hydroxyethylphosphines.

It is another object of the present invention to provide such a process which makes available relatively pure product.

These and other objects are obtained by a method for the preparation of 2-hydroxyethylphosphines comprising the steps of (1) the reaction of a phosphine having the structural formula

where R and R' are hydrogen, alkyl, aryl, cycloalkyl or aralkyl, with an alkenyl carboxylate having the structural formula

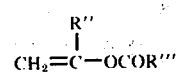

where R" is hydrogen or methyl, and R''' is a saturated aliphatic hydrocarbon radical of 1–17 carbon atoms, to form a 2-acyloxyethylphosphine, and (2) the subsequent alcoholysis or hydrolysis of said 2-acyloxyethylphosphine to the corresponding 2-hydroxyethylphosphine. Such method provides a convenient synthesis for the desired 2-hydroxyethylphosphines, in a satisfactory degree of purity such that no unusual or expensive methods of purification are required.

R and R' in the structural formula of the phosphine, above, preferably are hydrogen or an organic radical having fewer than eight carbon atoms. Such organic radicals are illustrated by methyl, ethyl, n-propyl, isopropyl, isobutyl, n-hexyl, 2-methylamyl, phenyl, o-tolyl, benzyl, cyclopentyl, cyclohexyl, and 3-methylcyclohexyl.

The alkenyl carboxylate preferably is vinyl acetate or isopropenyl acetate, although R''' may also be ethyl, n-propyl, n-heptyl, n-tridecyl, n-heptadecyl or the like.

The reaction to form the 2-acyloxyethylphosphine proceeds according to the equation

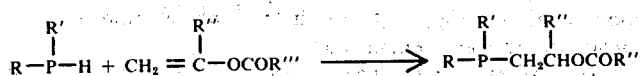

where R, R', R" and R''' are as identified earlier herein. A source of free radicals is necessary, to catalyze the reaction and this may be provided by a non-oxidizing initiator. Non-oxidizing initiators include principally organic peroxides and azo compounds having less than 30 carbon atoms, and of these the aliphatic initiators are preferred. Illustrative examples of such peroxides include di-tertiary-butyl peroxide, alpha, alphabis(tertiarybutylperoxy)diisopropylbenzene, diacetone alcohol peroxide, dicumyl peroxide, 1,1-di-tertiary-butyl-3,3,5-trimethylcyclohexane, and 2,5-dimethyl-2,5-(tertiary-butylperoxy) hexane.

The term "aliphatic" as used to describe these peroxides defines the peroxide linkages, i.e., the carbon atoms to which the peroxide group is attached. These carbon atoms are aliphatic carbon atoms. Thus, as illustrated above, an "aliphatic" peroxide may or may not contain aromatic groups. Dicumyl peroxide, for example, although it is an aromatic compound, is herein classified as an aliphatic peroxide because the carbon atoms to which the peroxide group is attached are

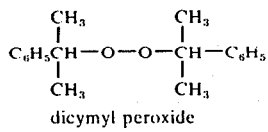

dicymyl peroxide aliphatic carbon atoms.

Illustrative examples of preferred azo compounds include alpha-cyano azo compounds, conforming to the structural formula

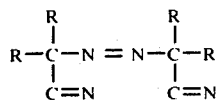

where R are the same or different alkyl or phenyl radicals having 1–6 carbon atoms. Azo-bis-isobutyronitrile (where all four R's are methyl) is particularly illustrative.

The amount of peroxide or azo compound used in the addition reaction may range from about 0.01% to about 5.0%. More than 5.0% can of course be used with no harmful effect, but with no added advantage. Ordinarily it is preferred to use from about 0.1% to about 2.0% of the peroxide or azo compound.

The reaction should be carried out in the presence of ultraviolet light, i.e., light having wavelength between 2000A. and 4000A. Light of wavelength between 2000A. and 2500A. is especially effective. The light serves to activate the free radical source, i.e., it causes decomposition of the nonoxidizing initiator to yield a free radical which in turn catalyzes the reaction of this first step. Ordinary sunlight will serve the purpose and in many instances is satisfactory. Preferably, however, an ultraviolet lamp is positioned alongside the reactor to provide relatively intense ultraviolet irradiation.

The temperature of this first step may range from about 10°C to about 50°C. Ordinarily the reaction is carried out at room temperature.

A solvent generally is used in this first step and is desirable so as to afford efficient mixing of the reactants. The solvent should of course be inert. Typical suitable solvents include benzene, toluene, heptane, methanol, ethanol, naphtha and the like.

When the reaction is completed, the acyloxyethylphosphine may be obtained merely by evaporating off any solvent leaving as a residue the desired acyloxyethylphosphine. It may be used as such in the second step of the method of the invention or, more conveniently, whatever solvent is used in the first step may simply be left in the reaction mixture to serve as a solvent in the second step.

The second step, i.e., conversion of the 2-acyloxyethylphosphine to the 2-hydroxyethylphosphine, may be accomplished either by alcoholysis or by hydrolysis. In the former instance, if an alkaline catalyst is used the alcoholysis medium should be substantially anhydrous whereas an acid catalyst permits an aqueous medium. Methanol is the most convenient alcoholyzing agent, forming a methyl acylate as a transesterification by-product. Sodium or potassium hydroxide or carbonate are suitable alkaline catalysts. Hydrochloric acid or sulfonic acid are suitable acid catalysts. Other alkaline and acid catalysts for this conversion are well known and the selection of a catalyst forms no significant part of the invention herein.

The conversion is effected merely by distilling away the methyl acetate (if methanol is the alcohol used) and excess methanol at a low temperature, viz., from about 20°C to about 50°C.

The hydrolysis reaction involves merely adding water plus an acid catalyst to the 2-acyloxyethylphosphine, then distilling away the water, again at a low temperature (as above).

The invention is illustrated in more specific detail by the following examples.

EXAMPLE 1

A solution of 258 g. (3.0 moles) of vinyl acetate and 0.5 g. of azo-bis-isobutyronitrile in 300 ml. of benzene is prepared and evacuated to the point at which the benzene begins to boil whereupon phosphine is bubbled in throughout a period of four hours. The mixture is exposed to sunlight all the while. Benzene is then removed at 25°C/15 min., care being taken to avoid any higher temperature so as to avoid polymerization, leaving as the residue a quantitative yield of tris-2-acetoxy ethylphosphine.

EXAMPLE 2

The procedure of Example 1 is repeated except that isopropenyl acetate is used instead of the vinyl acetate. In this case the desired tris-(acetoxypropylene)phosphine is obtained as a stable, colorless oil, merely by evaporating off the benzene.

EXAMPLE 3

A stirred solution of 11 g. (0.1 mol) of phenylphosphine, 21 g. (0.21 mol) of vinyl acetate, and 0.1 g. of di-tertiary-butyl peroxide in 50 ml. of benzene is prepared and irradiated as in Example 1. The temperature is maintained at 25°–30°C. The course of the reaction is monitored by scanning the P-H absorption at 2400–2450 cm.$^{-1}$ in an infrared cell. At the end of a two-hour period thee is no absorption in the region, indicating completion of the desired reaction. The benzene is removed by distillation, leaving the phenyl diacetoxy ethylphosphine as a colorless, viscous oil.

EXAMPLE 4

A stirred solution of 23 g. (0.2 mol) of cyclohexylphoshine, 17 g. (0.2 mol) of vinyl acetate and 0.1 g. of azobis-isobutyronitrile in 100 ml. of benzene is prepared and irradiated with ultraviolet light as in Example 1. The temperature is maintained at 25°–30°C. The course of the reaction is followed by observation of the disappearance of the infrared absorption for the vinyl group at 1650 cm.$^{-1}$ After three hours this absorption has disappeared completely and the P-H absorption has shifted from 2450 to 2425 cm.$^{-1}$ indicating conversion of the primary

absorption to the secondary >P—H.
Thus:

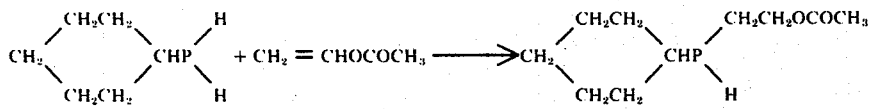

To this secondary phosphine intermediate product there is added 18 g. (0.21 mol) of methyl acrylate plus an additional 0.1 g. of azo-bis-isobutyronitrile and irradiation continued under the above conditions for another two hours at which point a scan of the infrared absorption spectrum of the reaction mixture shows the disappearance of the P-H absorption. Removal of the benzene by distillation leaves behind the cyclohexyl-2-acetoxyethyl-2-carbomethoxy ethylphosphine as a colorless, viscous oil.

EXAMPLE 5

A solution of 11 g. (0.1 mol) of phenylphosphine, 8.6 g. (0.1 mol) of metyl acrylate, 8.6 g. (0.1 mol) of vinyl acetate, and 0.1 g. of azo-bis-isobutyronitrile in 50 ml. of benzene is prepared and irradiated as above with stirring at 25°–30°C for two hours. At this point a scan of the infrared absorption spectrum of the product mixture shows the absence of all P-H absorption. NMR examination shows 90% of the product to be the phenyl-2-acetoxyethyl-2-carbomethoxy ethylphosphine.

EXAMPLE 6

A solution of 58.4 g. (0.2 mol) of tris-2-acetoxy ethylphosphine in 150 ml. of methanol is poured with stirring into 100 ml. of 37% aqueous hydrochloric acid, care being taken by means of external cooling to keep the temperature below 40°C. The resulting tris-2-hydroxyethylphosphine solution is warmed slightly at reduced pressure to distill away the methanol and any methyl acetate, leaving the desired product as a clear, viscous oil.

EXAMPLE 7

A 51 g. (0.2 mol) sample of phenyl bis-(2-acetoxyethyl)phosphine prepared as in Example 3 is hydrolyzed to the corresponding phenyl-bis-(2-hydroxyethyl)phosphine by the procedure of Example 6.

EXAMPLE 8

A solution of 58.4 g. (0.2 mol) of tris-2-acetoxyethylphosphine in 100 ml. of methanol is treated with 0.5 g. of sulfuric acid, then stripped of the excess methanol and methyl acetate (formed in the alcoholysis reaction). The residue, a viscous, light yellow oil, is the desired tris-2-hydroxyethylphosphine.

It will be noted, in Examples 4 and 5, that a 2-acyloxyethylphosphine containing a carbomethoxy (derived from methyl acrylate) group is prepared. Cleavage of such a compound results in a hydroxymethyl carboxylic acid, according to the following equation:

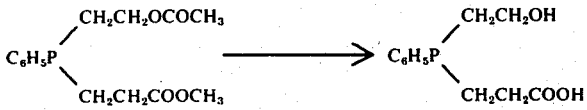

Care must be taken in any such conversion to avoid polymerization of the product to form a polyester. On the other hand, such polyesters are useful materials and their preparation from the above hydroxyethyl carboxylic acid and analogous compounds is an additional advantage of the process of the invention.

All parts and percentages herein are by weight unless otherwise expressly stated.

We claim:

1. A process for the preparation of 2-hydroxyalkylphosphines comprising the steps of (1) the reaction of a phosphine having the structural formula

where R and R' are hydrogen, alkyl, aryl, cycloalkyl or aralkyl, with an alkenyl carboxylate having the structural formula

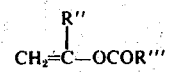

where R'' is hydrogen or methyl, and R''' is a saturated aliphatic hydrocarbon group of 1–17 carbon atoms, in the presence of (a) from about 0.01% to about 5.0% of a non-oxidizing aliphatic initiator having less than 30 carbon atoms, and (b) light having a wave length between 2000A. and 4000A., at a temperature which ranges from 10°C to about 50°C, to form a 2-acyloxyphosphine, and (2) the subsequent alcoholysis or hydrolysis of said 2-acyloxyalkylphosphine to the corresponding 2-hydroxyalkylphosphine.

2. The process of claim 1 wherein R and R' are hydrogen.

3. The process of claim 1 wherein R is phenyl.

4. The process of claim 1 wherein the alkenyl carboxylate is a vinyl carboxylate.

5. The process of claim 1 wherein the alkenyl carboxylate is vinyl acetate.

6. The process of claim 1 wherein step (2) is an alcoholysis reaction carried out under substantially anhydrous conditions.

7. The process of claim 6 wherein the alcoholysis reaction is facilitated by the presence of an alkaline material.

8. The process of claim 1 wherein step (2) is a hydrolysis reaction carried out under acidic conditions.

* * * * *